United States Patent
Dudkiewicz et al.

(10) Patent No.: US 6,781,704 B2
(45) Date of Patent: Aug. 24, 2004

(54) AUTOMATIC INSTALLATION AND PROCESS FOR TAKING MEASUREMENTS AND ACQUIRING SHAPES

(75) Inventors: Gilbert Dudkiewicz, Ruelisheim (FR);
Pascal Keiter, Hirtzfelden (FR);
Philippe Guerlain, Bennwihr (FR);
Franck Noel, Urschenheim (FR)

(73) Assignee: Telmat Industrie (Societe Anonyme), Soultz (FR)

( * ) Notice: Subject to any disclaimer, the term of this patent is extended or adjusted under 35 U.S.C. 154(b) by 284 days.

(21) Appl. No.: 09/988,254

(22) Filed: Nov. 19, 2001

(65) Prior Publication Data

US 2002/0126295 A1 Sep. 12, 2002

(30) Foreign Application Priority Data

Nov. 20, 2000 (FR) .......................................... 00 14963

(51) Int. Cl.⁷ .............................................. G01B 11/24
(52) U.S. Cl. ........................................ 356/603; 356/605
(58) Field of Search ........................... 356/2, 602, 603, 356/605, 613; 250/559.22

(56) References Cited

U.S. PATENT DOCUMENTS

| | | | | |
|---|---|---|---|---|
| 4,406,544 A | * | 9/1983 | Takada et al. | ............... 356/612 |
| 4,679,076 A | * | 7/1987 | Vikterlof et al. | ............ 348/142 |
| 4,786,925 A | * | 11/1988 | Landwehr | .................... 396/14 |
| 5,850,290 A | * | 12/1998 | Horiguchi et al. | .......... 356/602 |

FOREIGN PATENT DOCUMENTS

EP      0 683 379 A1    11/1995

* cited by examiner

*Primary Examiner*—Hoa Q. Pham
(74) *Attorney, Agent, or Firm*—Young & Thompson (57) ABSTRACT

An automatic and autonomous installation for taking measurements and acquiring three-dimensional shapes of subjects, particularly in the form of a booth adapted for human subjects, includes units for projecting light fringes, for taking rapid views, and for controlling the installation and processing the acquired views. The units for projection and taking views are gathered in one or several acquisition heads with a device generating a temporary wall of light opposite the acquisition heads.

18 Claims, 9 Drawing Sheets

Fig_10A  Fig_10B

Fig_10C

Fig_10D

Fig_10

AUTOMATIC INSTALLATION AND PROCESS FOR TAKING MEASUREMENTS AND ACQUIRING SHAPES

BACKGROUND OF THE INVENTION

The present invention relates to the field of taking measurements and acquiring representations of subjects, in particular of human subjects, and has for its object an automatic installation for taking measurements and for acquiring shapes of subjects, as well as a process permitting automatically carrying out these operations.

DESCRIPTION OF THE RELATED ART

Different systems of acquisition of three-dimensional shapes of subjects and taking measurements, particularly for their classification, already exist, such as for example those disclosed by GB 2159943 and EP0 524 119.

However, these known apparatus and devices all have one or several of the following drawbacks: complicated structure, impossibility of carrying out precise and realistic three-dimensional reconstructions of the subject, necessity for careful standardization before each acquisition or after each modification of position of the means for taking views, insufficient protection against parasitic light and consequent reduced reliability of the measurements, impossibility of simultaneous and correlative use of several views of the same subject given the duration of acquisition and the movements of the subject during these intervals, acquisition of partial information because of the color and nature of the clothing worn by the subject, the need to turn or cause the subject to turn to acquire various views and hence the unreproducibility of conditions of taking identical views, the need to acquire, process and store a large mass of data to supply precise data and the production of a virtual three-dimensional reproduction of the subject, not entirely automatic process, particularly as to standardization.

SUMMARY OF THE INVENTION

The present invention particularly has for its object to overcome at least certain ones of these drawbacks and certain ones of the mentioned limitations.

It has particularly for its object to provide a system and process permitting taking measurements and acquiring three-dimensional shapes of a subject in an automatic, rapid, reliable and precise manner, without requiring view taking devices that are too complicated or processing and storage means of very great capacity, becoming free from the interference of ambient light, color and the nature of the clothing worn by the subject and careful and repetitive standardization procedures with manipulation of standard objects.

To this end, the present invention has for its object an installation for the automatic acquisition of three-dimensional shapes and for taking measurements of subjects, particularly in the form of a booth adapted for human subjects, comprising at least one unit for projecting fringes, in particular light fringes, and at least one unit for taking views rapidly, as well as a control unit for the installation and processing of the acquired views, characterized in that said units for projection and taking of views are gathered into one or several acquisition heads and in that said installation also comprises, on the one hand, several fixed markers or reference points and several surfaces for reference projection surrounding the acquisition and measurement zone receiving the subject to be acquired and located in the field of vision of the unit or each of the units for taking views and, on the other hand, a means for generating a temporary wall of light opposite said at least one acquisition head or each of said acquisition heads relative to the acquisition zone.

It also has for its object an automatic process for the quasi-instantaneous acquisition of three-dimensional shapes and for taking measurements of subjects, in particular human subjects, particularly by means of the above installation, characterized in that it consists essentially in placing or causing to be placed a subject at the level of an acquisition zone, this zone comprising markers and reference projection surfaces, located in the fields of view of acquisition heads of views of said subject and constituting permanent standardization references, carrying out the acquisition of a so-called face view comprising, on the one hand, taking a first image of a face view of the subject by means of a first unit for taking views in synchronism with illumination creating a wall of light behind the subject by means of a first means for generating a wall of light, for the acquisition of a first contour by silhouette, and, on the other hand, taking a second front view of the subject by means of said first unit for taking views in synchronism with the projection of a network of horizontal fringes by means of a first projection unit on the front surface of the subject, then carrying out the acquisition of a so-called rear view comprising, on the one hand, taking a first rear view of the subject by means of a second unit for taking views in synchronism with illumination creating a wall of light in front of the subject by means of a second generating means for a light wall, for the acquisition of a second silhouette contour and, on the other hand, taking a second rear image of the subject by means of said second unit for taking views in synchronism with the projection of a network of horizontal fringes by means of a second projection unit on the rear surface of the subject and, finally, processing, by means of a suitable control and processing unit, the images and views acquired by correlation and exploitation of the different information supplied by them for the constitution of a three-dimensional representation of the subject of the extraction of measurements and/or of the classification of the subject in one or more predefined categories.

BRIEF DESCRIPTION OF THE DRAWINGS

The invention will be better understood from the following description, which relates to a preferred embodiment, given by way of non-limiting example, and explained with reference to the accompanying drawings, in which.

DESCRIPTION OF THE PREFERRED EMBODIMENTS

As shown particularly in FIGS. 1, 2, 3 and 6 of the accompanying drawings, the automatic installation 1, particularly in the form of a booth adapted for human subjects 2, comprises at least one unit 4 for the projection of fringes, in particular light fringes, and at least one unit 5 for rapidly taking views, as well as a control unit 6 of the installation for processing acquired views, integrated with or separated from said installation 1.

According to the invention, the units 4, 5 for projection and taking views are gathered in one or several acquisition head or heads 3 and said installation 1 also comprises, on the one hand, several markers or fixed reference points at 7 and several reference projection surfaces 8, for example planes, surrounding the acquisition and measuring zone 9 receiving the subject 2 to be acquired and located in the field of view of the unit or of each of the units 5 for taking views and, on the other hand, a means 10 for generating a temporary light wall opposite said at least one acquisition head 3 or each of the acquisition heads 3 relative to the acquisition zone 9.

The light walls permit masking the structure of the booth 1 to the image and supplying a sufficient luminosity to show the contours despite the ambient luminosity.

Figures 1, 1A:
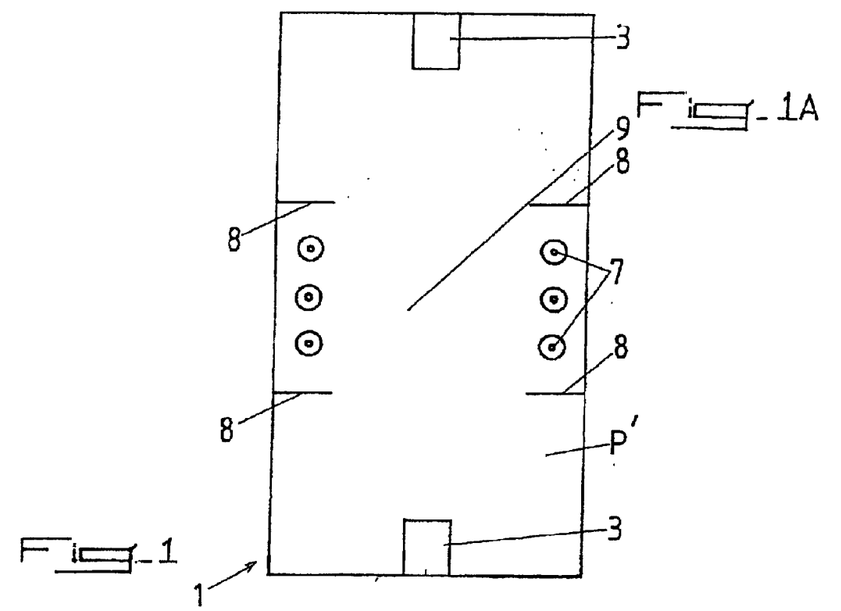
FIGS. 1A and 1B are schematic views by transparency from the top and side of an installation according to a first preferred embodiment of the invention.
Figure 2:
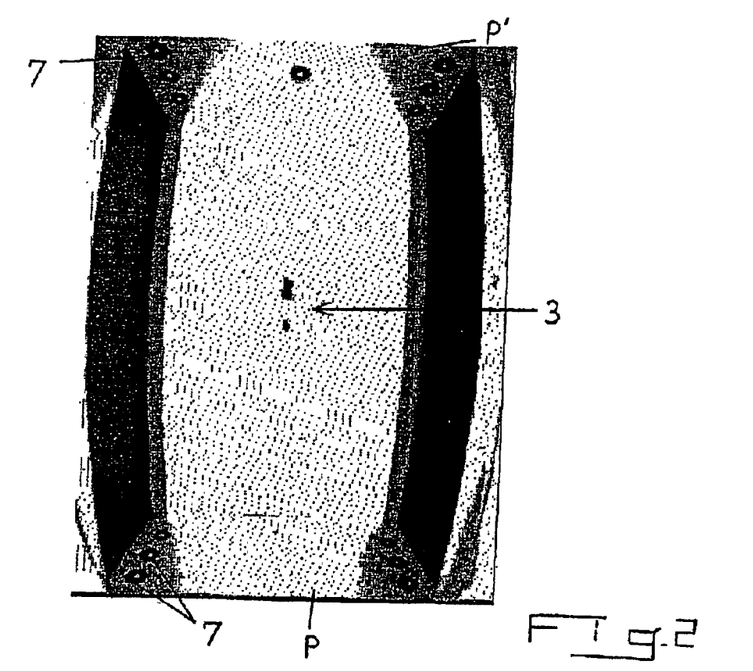
FIG. 2 is a representation of the image through the optics of one of the devices for taking views, forming a part of the installation shown in FIG. 1.
Figure 3:
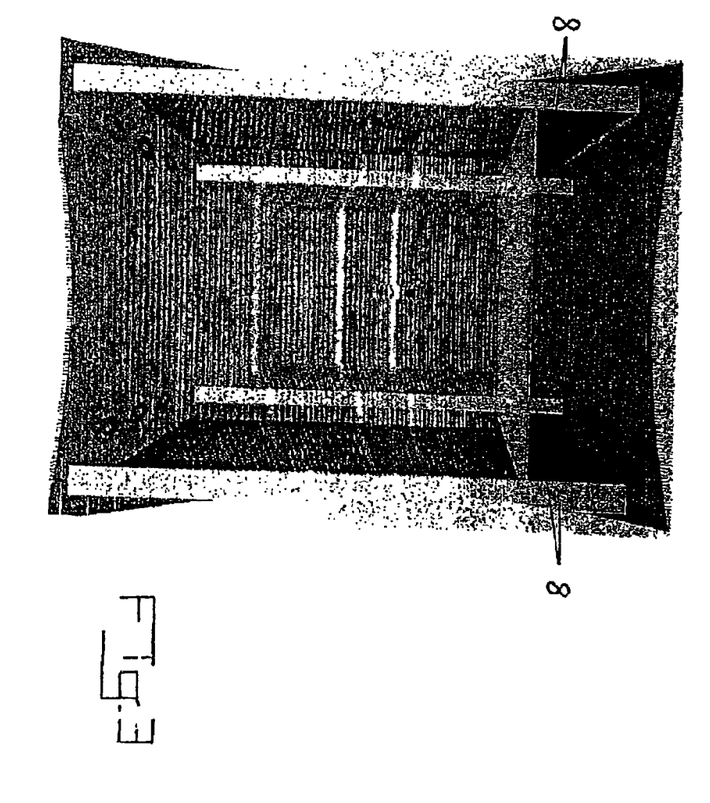
FIG. 3 is a representation similar to that of FIG. 2 with projection of the network of fringes according to the invention and correction of certain image deformations.

According to a first characteristic of the invention, resulting particularly from FIGS. 1, 2 and 3, the acquisition zone 9 consists in a substantially parallelepipedal volume, the markers 7 being disposed at known places of the control and processing unit 6 according to several lateral alignments in the direction of taking the view and in two spaced parallel planes P, P' delimiting the upper and lower surfaces of said volume 9 and the reference projection surfaces 8, not deforming and preferably flat, consisting of vertical scales connecting the two planes P, P' mentioned above at the level of the four vertical edges of the acquisition zone 9, the information supplied by the markers 7 and the projection surfaces 8 on the different views being used by the unit 6 upon each acquisition for the standardization of the installation 1.

The markers 7 could for example consist of discs or dark circular plates having a motif in the form of a target or of a mark or a central tablet that is lighter and their alignment could for example extend between the scales 8, outside the central portion of the zone 9 receiving the subject 2, so as not to be hidden on the images.

Moreover, the arrangements or a number of different markers 7 in the plane P and P' permit the unit 6 to recognize without difficulty the orientation of the acquired image.

The markers 7, preferably disposed symmetrically relative to a vertical medial plane of the booth, will be detected automatically by the installation 1 upon each startup and in the course of each acquisition session and will permit determining the assembly of the extrinsic parameters of the units for taking views 5 to be taken into account by the control and processing unit 6 for the control of the installation 1 and the use of the views.

The scales 8, preferably in the form of elongated plates seen in the similar arrangements by units 5, permit, because of their spatial distribution at the corners of the zone 9, locating and identifying each fringe plane (see FIG. 3) and can if desired serve as flat uprights to support the structure of the booth 1 and to define the passages to enter and leave this latter.

Said markers 7 and scales or uprights 8 permit standardization and precise acquisition because of their location at the periphery of the acquisition zone 9, and permit carrying out a standardization calibration step at each acquisition of a view, their consideration by the unit not being hindered by the subject 2.

Thus, the taking of a view carried out by the installation 1 is not reduced to taking a photo in the common sense of the term, because it is necessary to identify the transformation entering into play during passage of the real world to the image world and to correct the deformations introduced into the image acquired by the optical system.

Once the image is corrected, it is possible to extract from it the shape necessary for a portion of taking the measurement as well as the fringes projected on the body which will serve for the three-dimensional reconstruction of the surface.

The fringes are then coupled to the parameters of transformation identified during taking the views so as to reconstitute the three-dimensional image of the photographed surface.

The good operation of this process resides in the good mathematical modeling of the successive transformations undergone by the image of the person during taking the photo. It is thus necessary to determine how the passage from the real world to the image world takes place, then from the image world to the real world.

The information of the three-dimensional real world is acquired by at least one unit 5 of the digital video camera type of the CCD type (Charge Coupled Device), associated with an objective adapted to cover all the acquisition volume 9 without movement.

Thanks to the mentioned standardization means, the unit 6 is able to correct the radial distortion of the image as well as the rotation of the camera relative to the references in the booth. At the end of standardization in the factory and standardization on site, the working images obtained are directly usable to carry out computations of length or positioning of the image.

The parameters of the camera model being fixed, it is possible to obtain the image coordinates (u; v) of any point (x; y; z) in the seam. Conversely, it is possible to compute the coordinates (x; y; z) of a point on the seam based only on its image coordinates (u; v) and an indication of its positioning along z.

The units 5 for taking views, preferably in the number of at least two, will be disposed in configurations permitting taking into account all or almost all of the surface of the body of the subject 2 without movement of this latter, nor of said units 5.

Figure 1B:
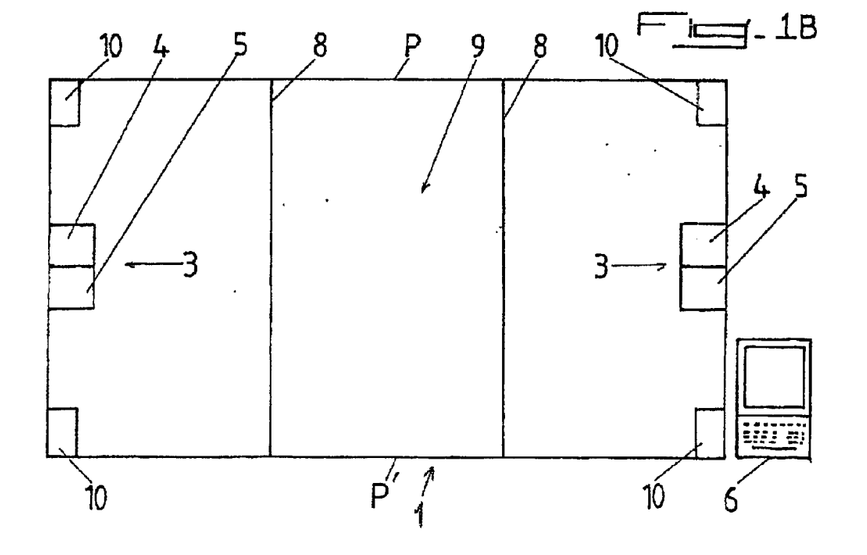

According to a preferred embodiment of the invention and as shown in FIGS. 1A and 1B of the accompanying drawings, the installation 1 comprises two acquisition heads 3 located in opposition on opposite sides of the acquisition zone 9, and each of said heads 3 encloses in its field of vision all the markers 7 and the projection surfaces 8. Moreover, with each of these heads 3 is associated one or more means 10 for the generation of a corresponding light wall, the arrangement of the markers 7 and/or projection surfaces 8 permitting determining the upper, lower and side ends of the acquisition zone 9, as well as the orientation of this latter.

Said units 3 will preferably be disposed at about midheight, such that the second unit 3 will be covered during taking a view by the first unit 3 and vice versa and whether centered relative to the volume 9.

Figure 13:
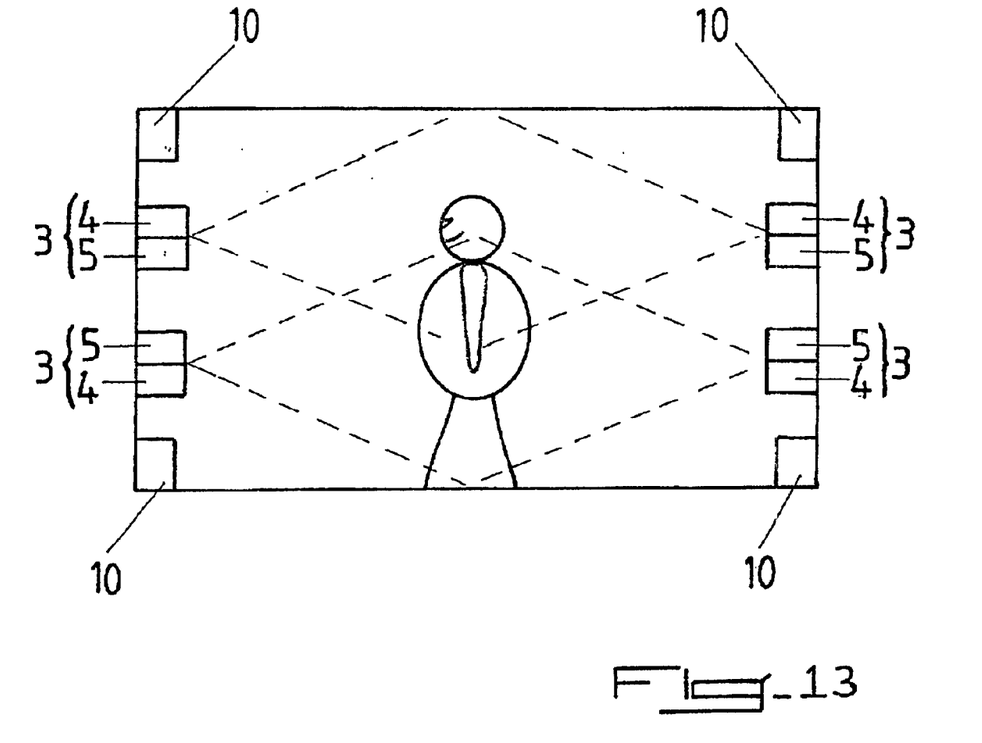
FIGS. 13 and 14 show schematically respectively in side view and in top view, modifications of the embodiment of installation shown in FIG. 1, and, FIG. 15 is a process diagram showing the progress of a session of acquisition using the installation according to the invention in the form of a booth for human subjects.

According to a modified embodiment of the invention, shown in FIG. 13 of the accompanying drawings, the installation 1 can comprise four acquisition heads 3 gathered into pairs of heads located in opposition on opposite sides of the acquisition zone 9. One head, located in a lower position, of each of the pairs of mentioned heads, encloses within its field of projection and vision a lower portion of the acquisition volume 9 and the other head, located in an upper position, of each of said pairs of heads, encloses an upper portion of said volume 9, complementary and partially overlapping with the mentioned lower portion, said lower heads, respectively upper heads enclosing, moreover, the lower markers 7, respectively upper markers 7, and lower portions, respectively upper portions, of the reference projection surfaces 8.

Such an arrangement permits acquiring views with a greater definition and hence having views and representations that are more precise, the processing of the information being similar to that used in relation to two single acquisition heads 3, except for elimination of redundant information in the overlapping portions and an assembly of the lower and upper portions of the front and back views.

It will be noted in FIG. 13, that the relative arrangements of units 4 and 5 of the lower and upper heads of each pair are reversed.

According to two other modified embodiments of the invention, not shown in the accompanying drawings, the installation 1 can comprise either at least three acquisition heads 3, or at least three units 5 for taking views, disposed along Y and in the booth forming the installation 1, or at least four acquisition heads 3, for at least four units 5 for taking views, disposed along X in the booth forming the installation 1.

The three or four acquisition heads 3 could also consist of pairs of heads as described above for the arrangement in I.

These two modifications permit obtaining lateral (and not frontal) angles of view and hence gathering supplemental information concerning the side surfaces of the subject 2.

Figure 14:
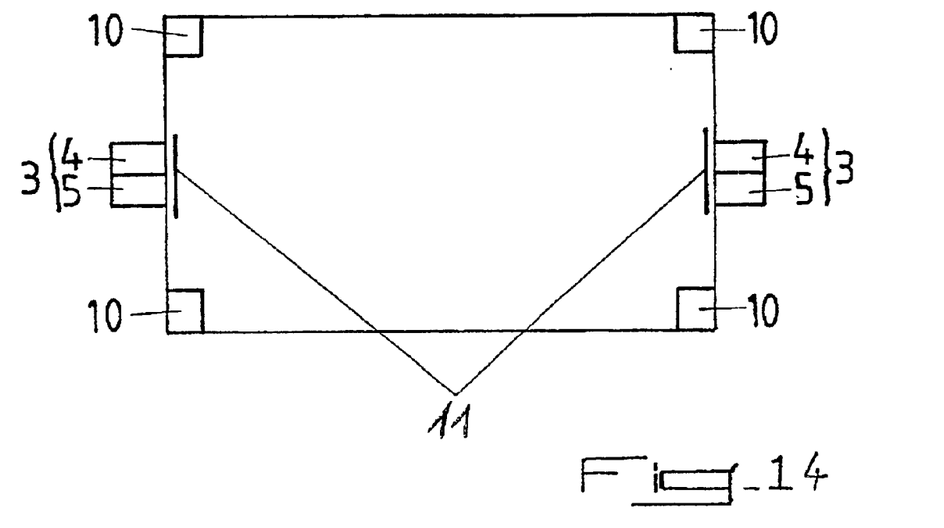

Moreover, the units 4 and/or 5 could be mounted in the booth 1 (FIGS. 1 and 13) or be mounted outside this latter by being separated from the interior of the booth by a portion of a transparent partition 11 (FIG. 14).

Figures 4, 4B:
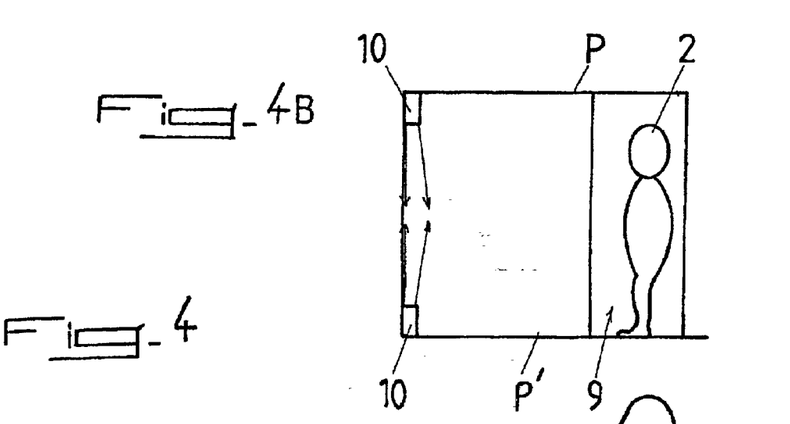
FIGS. 4A and 4B are fragmentary schematic views in side elevation of an installation according to the invention comprising two modified embodiments of a means for generating a light wall.

According to one characteristic of the invention, shown in FIGS. 1B and 4 of the accompanying drawings, the means 10 for generating the light wall consist of electronic flashes whose triggering is synchronized with that of the unit or units 5 for taking views which is opposed relative to the acquisition zone 9, this unit or units 5 each consisting in a digital video camera, for example of the CCD type.

This arrangement permits, by centering the period of acquisition of the cameras 5 relative to the interval of illumination of the flashes 10, to cancel the influence of the ambient light for taking images of contours, limiting the consumption of energy and not disturbing the acquisition of the images obtained during projection of the fringes.

Figure 4A:
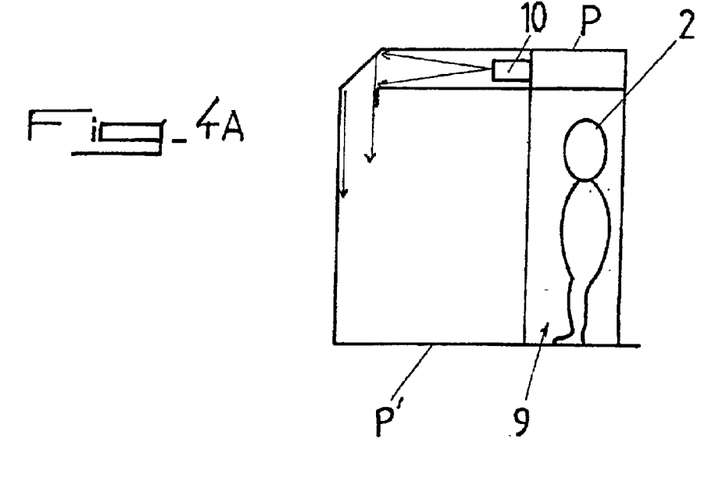
Figure 5:
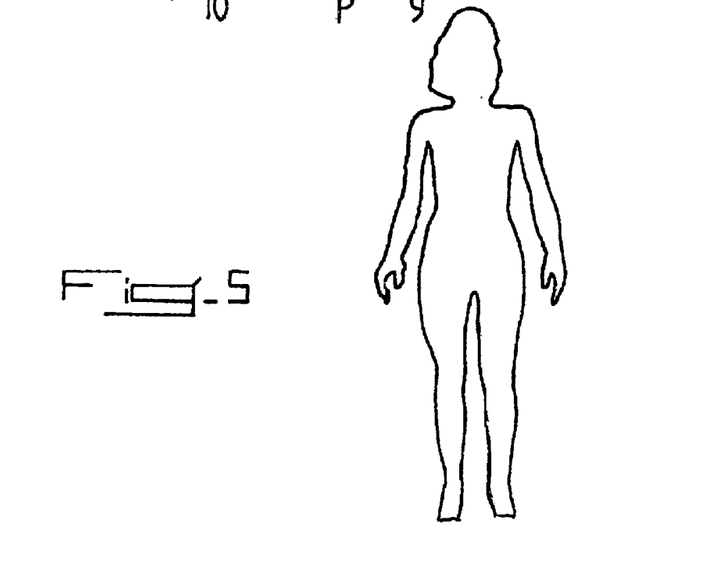
FIG. 5 is a contour representation in silhouette of a female human subject in a front view obtained with the installation according the invention.
Figure 6:
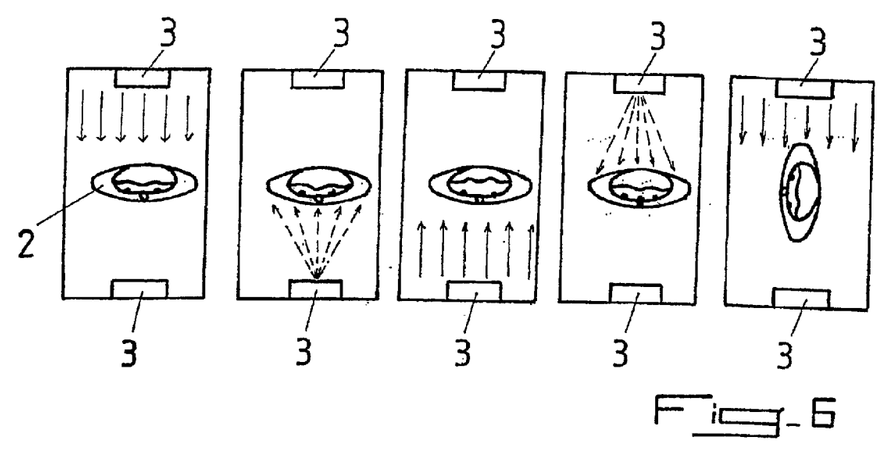
FIG. 6 shows schematically the different phases of taking possible views according to the process of the invention.

FIG. 4A shows an embodiment of each means 10 in the form of a flash disposed in the upper portion of the booth 1 and whose light flux is deflected by an inclined surface to be grazing the back of the booth and FIG. 4B shows an embodiment, similar to that of FIG. 1, in which each means 10 is formed by two opposite flashes disposed at two opposite ends of a back of the booth 1, triggered simultaneously and whose emitted light flow is directed in the direction of the other flash.

Similarly, the alternately black and white fringes are produced by units 4 by means of electronic flashes associated with projection objectives without geometric deformation, for example of the aspherical type, and synchronized as to triggering with the units 5 for taking views of the corresponding acquisition heads 3, the black fringes having a width greater than that of the white or light fringes, the ratio of the black fringe width to the white fringe width being comprised between 1.1 and 1.5, preferably about 1.3.

This latter arrangement permits obtaining a good contrast between the black and white rays without saturating the cameras 5.

So as to be able to guarantee identification and reliable location of the different fringes, no matter what the deformations introduced by the optics and by inequalities in the configuration of the surface of the subject 2 to be acquired three-dimensionally, each of the projected horizontal fringe networks comprises at least two white fringes FR1, FR2, FR3 that are mutually spaced apart, having widths substantially greater than those of the other fringes, preferably two or three times as great, and serving as reference fringes for marking and identification of the other fringes.

Figure 7A:
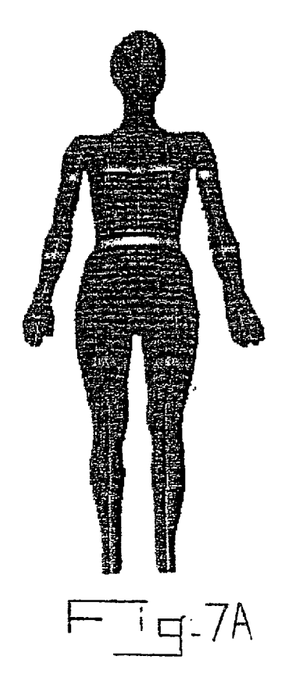
FIGS. 7A to 7C show respectively the image acquired by projection of fringes after isolation, the image obtained after extraction of the ends of the signal along vertical parallel lines and the image obtained after identification of real fringes or fragments of fringes and suppression of artifacts.
Figure 7B:
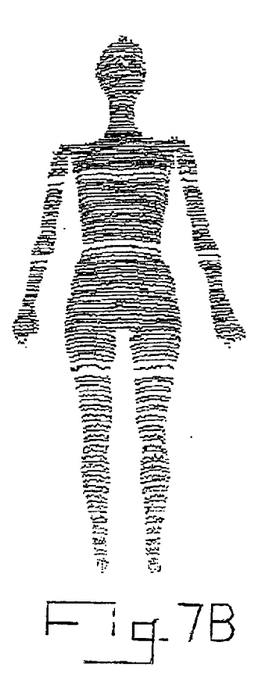
Figure 7C:
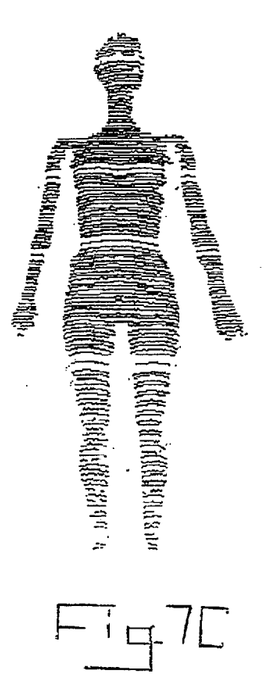
Figure 8:
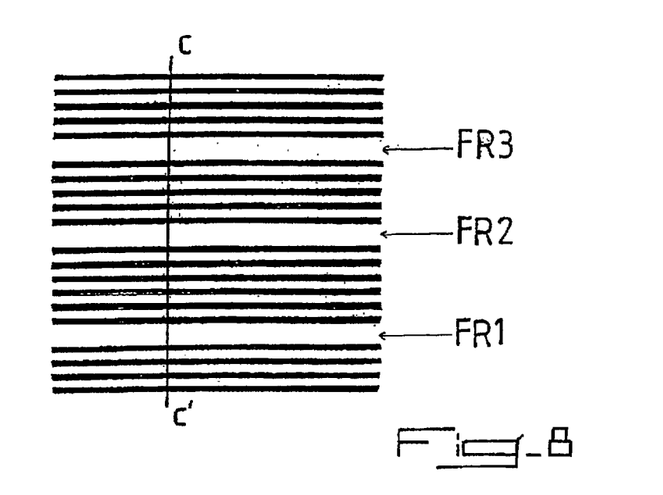
FIG. 8 is a theoretical representation of the network of projected fringes.

Preferably, as shown in FIGS. 3, 7 and 8, each of the fringe networks comprises three reference fringes FR1, FR2, FR3 disposed asymmetrically in the pattern of the network in question and/or with different mutual spacings, one of said reference fringes FR1 being disposed for a projection at about a third of the height of the volume formed by the acquisition zone 9 and at least one other FR2 for a projection at about two-thirds of the height of the volume formed by said zone 9.

In the case of a human subject 2, one of the reference fringes FR1 will thus be located for a projection at the level of the legs of the subject 2 placed in the acquisition zone 9 and at least one other FR2 for a projection between the wrists and shoulders of said subject 2.

The units 4, 5 and 6, as well as the constituent elements of the structure of the booth (framework, base, white panels constituting the back and the planes P and P', . . . ), are known to those skilled in the art and do not require a more detailed description, their particular characteristics having been indicated above.

The installation 1 will moreover comprise means for the detection of a subject 2 and for the determination of its position (if desired the necessary view is taken by the acquisition heads 3 and the use for this purpose by the unit 6), associated with means for giving sonic messages adapted to guide and inform the subject, permitting making the operation of the installation entirely automatic and autonomous.

The preliminary verification of the overall positioning is a process which qualifies the position of the person within the booth and which thus diagnoses whether the acquisition is potentially good to carry out an extraction of the contours and surfaces. This process also diagnoses the improper positions of the persons, which permits if desired giving out a sonic message suitable to correct the position of the person.

There also exists an expertise after the acquisition, which determines whether the surfaces and the contours acquired are of sufficient quality to start an extraction of measurements.

Said installation could, as the case may be, also be provided with a communication interface permitting the subject 2 to dialog with the unit 6, for example to determine the destination of the measurements or the form of their edition (slip, magnetic card, teletransmission, . . . ).

The invention also has for its object an automatic process for the quasi-instantaneous acquisition of three-dimensional shapes and taking measurements of subjects, in particular humans, particularly by means of the installation 1 described above, comprising two opposed acquisition heads 3, characterize in that it consists essentially in placing a subject 2 in an acquisition zone 9 located in a booth 1 or the like, this subject 2 being disposed in a given posture and/or position and this zone 9 comprising reference marks 7 and reference projection surfaces 8, located in the field of vision of acquisition heads 3 of views of said subject 2 and constituting permanent standardization references, to carry out the acquisition of a front view comprising, on the one hand, taking a first image in the so-called front view of the subject 2 by means of a first unit 5 for taking views in synchronism with illumination creating a wall of light behind the subject 2 by means of a first means 10 for generating a wall of light, for the acquisition of a first contour in silhouette and, on the other hand, taking a second front image of the subject 2 by means of said first unit 5 for taking views in synchronism with the projection of a network of horizontal fringes by means of a first projection unit 4 on the front surface of the subject 2, then carrying out the acquisition of a so-called rear view taken in a direction opposite the direction of taking the mentioned front view, said acquisition comprising, on the one hand, taking a first image as a back view of the subject 2 by means of a second unit 5 for taking views in synchronism with illumination creating a wall of light in front of the subject 2 by means of a second means 10 for generating a wall of light, for the acquisition of a second contour in silhouette and, on the other hand, taking a second rear image of the subject 2 by means of said second unit 5 for taking views in synchronism with the projection of a network of horizontal fringes by means of a second projection unit 4, on the rear surface of the subject 2, and, finally, processing, by means of a suitable control and processing unit 6, the images and the views acquired by correlation and exploitation of the different information supplied by them for the construction of a three-dimensional representation of the subject 2, and the extraction of measurements and/or the classification of the subject 2 in one or more predefined categories.

In the case of a human subject, the most favorable position could be indicated on the floor by marks and the ideal posture for acquisition is the standing position, with the arms slightly spaced from the body and the legs spaced apart.

The series of acquisition steps indicated above can be modified by carrying out, for example, successively the two images in silhouette, then the two fringe images.

The extraction of the silhouette contours could for example be carried out by a method of following the contour based on the gradients of luminous intensity of the acquired image (known to those skilled in the art).

Moreover, the images acquired following the projections of the network of fringes are, to facilitate their processing, cropped by elimination of the fragments of fringes located beyond the contours.

Preferably, the process also consists in carrying out, in the course of each acquisition of a view, the step of automatic standardization based on information supplied by the markers 7 and the reference projection surfaces 8 on the different images collected and used by the unit 6.

Preferably, the projected fringe networks each comprise luminous reference fringes FR1, FR2, FR3 distributed asymmetrically in the design of the network in question and having a width substantially greater than that of the other fringes.

Moreover, the taking of the images is carried out in a sequential manner over a time interval of acquisition which is completely sufficiently reliable to avoid any taking account of possible movement of the subject 2.

The mentioned processing operation consists particularly in isolating the surface images acquired by projection of the fringes by means of corresponding images acquired in silhouette, then displaying and localizing the fringes on the images by spatial filtering, by determining, analyzing and locating, and if desired by extrapolation, the upper and lower ends of the signal collected along a plurality of vertical lines, then in identifying the different fringes, as the case may be after recomposition from fragments of fringes, and particularly the reference fringes or fragments of reference fringes FR1, FR, FR3, numbering these fringes or reference fragments and finally propagating the numbering to the assembly of fringes contained in the isolated representations of the subject 2.

The identification of the fragments of fringes consist in establishing vertical adjacency relations between consecutive fragments in the vertical direction of the views, and qualifying these relations, with identification or not of fringes or fragments of real fringes, as a function of the length or size of overlap between two adjacent fragments, of the mean distance between two adjacent fragments, and of the respective colors of these latter.

Moreover, the propagation of the numbering of the fringes, after identification and numbering of the reference fringes FR1, FR2, FR3, consists in defining a chain of reference starting from the top of each representation of the subject 2 on the images of surfaces in the form of images with isolated fringes and extending downwardly and/or along the sides to the ends of the different ramifications of the representation of the subject 2.

Finally, the constitution of the three-dimensional representation consists, after identification and numbering of the images of the isolated surface acquired by projection of the fringes in the front view and in the rear view, in generating representations, in the form of stacks of slices, of different separate and complementary zones of the subject 2, zones predetermined by means of characteristic points localized on the contours obtained from the silhouette views, in assembling among others, for each of the mentioned separate zones, the two corresponding half shells representing the front and rear view, in the form of stacks of slices, a given zone of the subject 2 and, finally, in reconstituting a total three-dimensional volumetric representation by assembling the stacks of slices representing the different separate zones of the subject 2.

To verify the exactitude of the three-dimensional restitution and the computed measurements, it can moreover be provided to carry out, as the case may be after rotation by 90° of the subject 2 about a vertical axis, the taking of a profile view by means of a view taking unit 3 triggered in synchronism with a means 10 for generation of a corresponding opposite wall of light, so as to acquire the silhouette contour of the subject 2 seen in profile.

There will be described hereafter with more precision, by way of example and with respect to FIGS. 3, 7, 8, 9, 10, 11A, 11B and 12, and with the installation 1 shown in FIGS. 1A and 1B, the operations of extracting fringes and three-dimensional reconstruction of a subject 2.

By preceding with several modifications taking account of the angles of taking of the view and of the number of units 5, this process could equally be used in relation to acquisition heads 3 disposed along X, along Y or along I with two pairs of heads, as described in the above modifications.

So as to obtain the three-dimensional reconstruction of the person to be measured, it is necessary to proceed to the three-dimensional reconstruction of each of the projected fringes.

This reconstruction supposes that the fringes be localized in the image and then identified in a unique manner relative to the design of the projected motif. These fringes are then placed in correspondence with their mathematical characteristics extracted during the standardization phase.

So as to facilitate the location of the fringes, there is carried out a first filtering, by not looking for fringes other than within the extracted contours, so as to reconstruct only the elements present in the body of the person.

Although a first level of filtering will be carried out, the location and then the identification of the fringes must be carried out.

Three problems can arise:

a fringe can be absent because poorly identified or unidentified, an element of the observed scene, an elastic on a garment for example, can be wrongly interpreted and confused with a fringe, several fringes can be joined particularly on pronounced reliefs of the body such as the bosom, the neck and the sides.

Figure 9A:
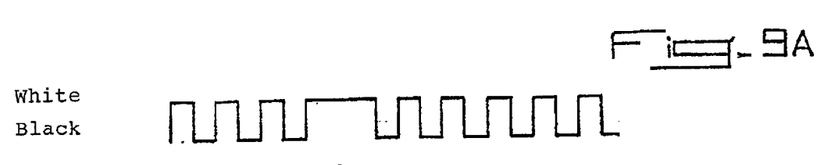
FIGS. 9A to 9C are fragmentary representations of the signal along line C–C' of FIG. 8 respectively at the moment of projection of the network of fringes, at the moment of optical acquisition of the image supplied by the network of projected fringes, and after sampling.

FIG. 8 shows a pattern of a network of fringes as theoretically projected and FIG. 9A the signal taken from a portion of the line C–C' of this projected design.

Figure 9B:
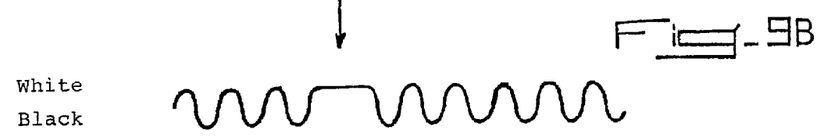

FIG. 9B shows the signal (along C–C' in part) as collected at the level of the cameras 5 and deteriorated by optical systems for the projection of fringes and the acquisition of images, after projection of the network of FIG. 9A.

Figure 9C:
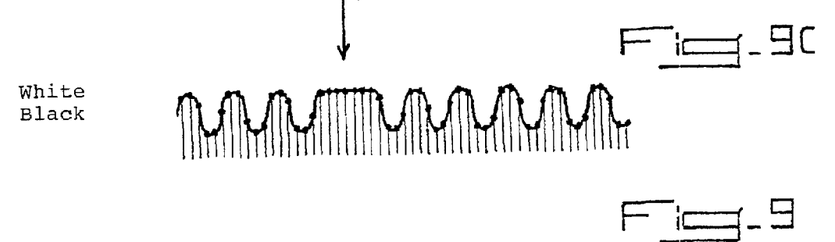

The signal of FIG. 9B is sampled by the cameras 5, or by a pixel, as shown in FIG. 9C;

To then locate the fringes, all the ends present in the image are located. Given that only the reconstruction of the surface of the subject is sought, only the fringes present within the extracted contour are located.

To do this, it is necessary to sweep the interior of the contour column by column so as there to locate the signal and then to recompose the fringes by associating the information from the processing of the columns.

The ends of the signal are located at the near pixel in the profile of the intensity because of the discrimination of the signal by the camera. So as to obtain a three-dimensional reconstruction of points of fringes detected as precisely as possible, it is imperative to locate very precisely said ends.

To do this, the theoretical ends are determined from gathered sampled information.

Having detected an end in the sampled signal, it is supposed that it, as well as its near neighbors, describe a continuous curve of the third order approximating the real signal (cubic approximation between four points).

After determination of all the local ends in all the columns or lines vertically cutting off the image with isolated fringes (minima=potential black fringes; maxima=potential white fringes), as shown in FIG. 7B of the accompanying drawings, it is necessary to recompose the fringes to which the predetermined ends belong.

To recompose the fringes, it is necessary to attempt to associate the ends of each column with the ends of the immediately adjacent columns.

The ends of two immediately adjacent columns can be associated only if they are of the same nature (they are both minimum or maximum). Moreover, given that a fringe appears in the image as being a series of contiguous points, the spacing between their ordinates must be of one pixel at most (given that the image is studied column by column, the interval of the abscissas is in any way one pixel).

This recomposition does not always permit obtaining continuous fringes, so we will speak of fragments of fringes. In practice, the fringes are fragmented when they appear on several portions of the body (for example, one fringe appearing on the arms and the bust is fragmented into three portions). The fragmentation can be more important by virtue of accidents of relief or texture.

The following step consists in identifying the fringes, particularly by eliminating the fringes corresponding to artifacts and not to real fringes, then to numbering them.

Figure 10A:
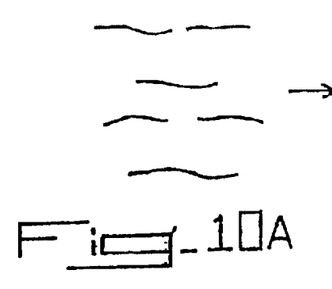
FIGS. 10A to 10D are schematic representations showing different steps in the operation of identifying fragments of fringes by means of the relationship of adjacency used in the scope of the process according to the invention.
Figure 10B:
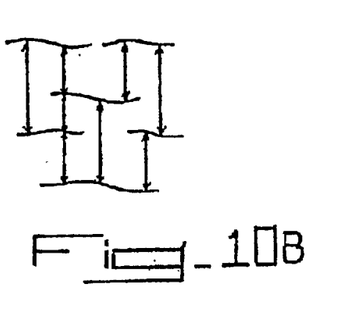

To this end, the process according to the invention uses, as already indicated above, the relationships of vertical adjacencies between the fragments of fringes (see FIGS. 10A and 10B).

The zone of overlap of a fragment with an adjacent fragment corresponds to the points whose abscissas are common to the points of the adjacent fragment.

From the zones of overlap of the different adjacent fragments, can be extracted a quantity of overlap for each of the adjacent fragments according to the formula:

Quantity of Overlap=length of overlap/length of the fragment.

Two adjacent fragments will not necessarily have between them the same quantity of overlap.

The mean distance from one fragment to one of its adjacent fragments corresponds to the mean of the distances between the fragments in the zone of overlap.

The color of adjacent fragments contributes to determining the number of fragments that may be lacking between the studied fragment and the adjacent fragments.

Figure 10C:
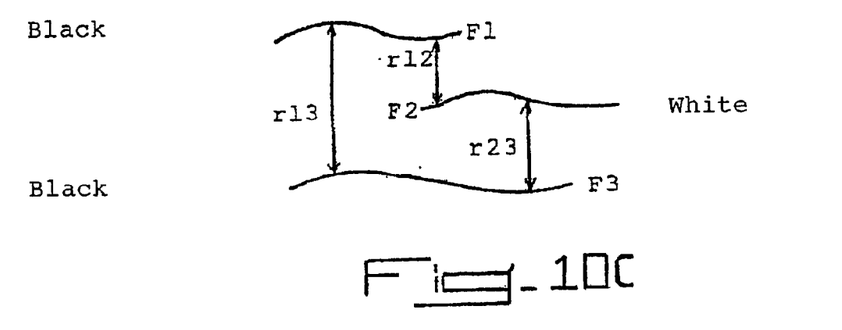

According to the schematic diagram of FIG. 10C, the fragment F3 is associated with the fragments F1 and F2 by adjacency relationships r13 and r23. Given that F1 and F2 are of different colors, it is certain that the difference in numbering between F1 and F2 is uneven. Similarly, the difference in numbering between F1 and F3 is even because the fragments are of identical colors.

Knowing the mean distance between two adjacent fragments, as well as the local statistical difference between two fragments, it is possible to make an estimation of the difference of numbering between these two fragments. To do this, we compute the ratio: R=mean distance/local statistical difference.

The most probable difference of numbering thus corresponds to the whole number closest to R whose parity is that determined according to the colors.

By way of example, let it be supposed that we have obtained the ratio R=1.7 between two adjacent fragments. If these two fragments are of identical colors, the difference of numbering between these two fragments will correspond to the even number closest to R, namely 2. If by contrast the fragments are of different colors, the difference of numbering will correspond to the odd number nearest R, which is to say 1.

The adjacency relationships between the fragments are then qualified so as to determine which differences of numbering are the more reliable. These qualifications depend on the importance of rounding from the difference, of the size of overlap of the fragment to its adjacent fragment, and even to the length of the fragment.

If the adjacent fragment is of relatively small size, the difference of numbering which is extracted from it is less reliable than if it were from a fragment of a more consequential length. The smaller the fragment, the greater the risk that it will represent a local disturbance such as shown for example in FIG. 10D which corresponds to a gluteal fold.

Figure 10D:
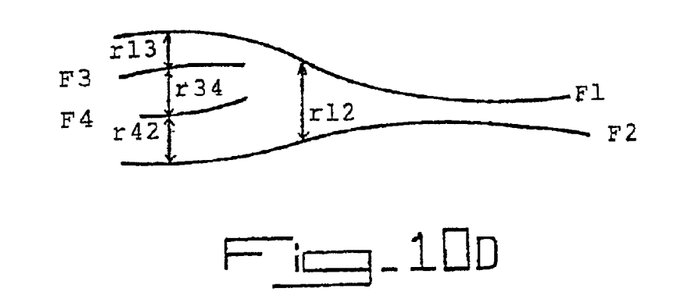

This method permits, in the example shown in FIG. 10D, confirming the fragment F2 as the successor to the fragment F1, the fragments F3 and F4 being quite likely accidental.

At this level of processing, there is used a relative sequencing of the fragments which permits at present establishing the number of each fragment by degrees.

The fragments of the same number will belong to the same fringe.

Then to establish the numbering, it is indispensable to have one or several identified fragments which will serve as references.

The first step in the numbering consists in creating, as a function of the contour, privileged paths of research of the fragments of the reference fringes which will be adaptable to the human morphology. The characteristic of these paths is to pass over zones from the corresponding image to portions that are supposed to be less disturbed of the body. There is thus avoided derangement by zones such as the bust and the gluteal folds. FIG. 7 shows an example of research paths.

On each of these paths, there are selected fragments which could be reference fragments. A reference fragment is a white fragment enclosed by two black fragments which are distant by a value nearly four times the distance between the mean fragment.

Among all the retained fragments, certain are selected even though they are not reference fragments, whilst others, which are reference fragments, are not selected for various reasons of signal degradation.

It is then necessary to filter the selection obtained, so as to eliminate the fragments which do not correspond statistically to the description of the design whilst possibly ameliorating the absence from the selection of one or the other reference fragment. The comparison of the selections of reference fragments obtained along various paths permits selecting the configurations which guarantee the coherence of the assembly of the numbering.

The reference fragments FR1, FR2 and FR3 being identified, it is then necessary to attribute to them their numbers as a function of the known data of the design. It remains at present to propagate the numbering of the assembly of the fragments from each of the reference fragments by following the adjacency relations.

During the numbering of a fragment by an adjacent fragment, a quality index of the numbering is also propagated. The quality index is computed as a function of the quality index of the adjacent fragment or from which the numbering arises, as well as a function of the quality of the adjacency relation. The quality index is a maximum for a reference fragment and degrades to the extent the numbering propagates.

The numbering attributed to a fragment can be different according to the adjacent fragments because their numbering does not arise from the same reference fragments and have not necessarily followed the same adjacency relationships. The fragment thus will keep the number given to it with the best quality.

This numbering operation having been accomplished, it is possible to proceed to the three-dimensional reconstruction of the subject 2.

The reconstruction of the subject 2, for example of the body of a human subject, consists in constructing a closed volume with the help of surface images from the front and the back. To do this, the principle is adopted of a body constituted by a stack of three-dimensional slices whose characteristics of height an inclination are the subject of parameters.

However, the points of the support fringes of the front and back surfaces are not points whose Y coordinate is constant, because of the relief of the body and of the angle of projection of the fringes.

To have the necessary slices, it is thus necessary to generate them from collected front and rear surface images.

To close the mentioned slices, the particular zones are isolated that divided the body of the human subject. To do this, there are injected a minimum of points characteristic such as the base of the neck, the crotch and below the arm. Once detected, these characteristic points serve to identify the bust, the arms, the legs and the head in these contours.

The points of the contours being expressed as image coordinates, there is no three-dimensional reconstruction concerning them, the fringes not being visible. However, having stored the image coordinates of the points of the surfaces, it is very easy to recognize the zone of origin of each point of the surfaces with the help of the contours.

To reconstruct the body with the help of a stack of slices, it is necessary, in the first instance, to generate slices pertaining to each zone of the body as mentioned, by separately processing the slices in the front surface and the rear surface. A slice in a surface is easily obtained by running through all the facets of the grid and by keeping the facets intersected by the plane of the slice.

Once the front and rear slices are extracted (see FIG. 11A), it is necessary to close them in the most natural manner possible. Thus, during acquisition by two heads 3 disposed in a I, a large surface located on the flanks of the person has not been acquired by the two heads 3 because it is not visible by these latter. So as not to close the body in a too abrupt manner, which would give false measurements, it is important to join the front and rear slices with the help of a curve respecting the initial shape of the body (recognition of the shape of the subject in the location in question).

Figures 11A, 11B:
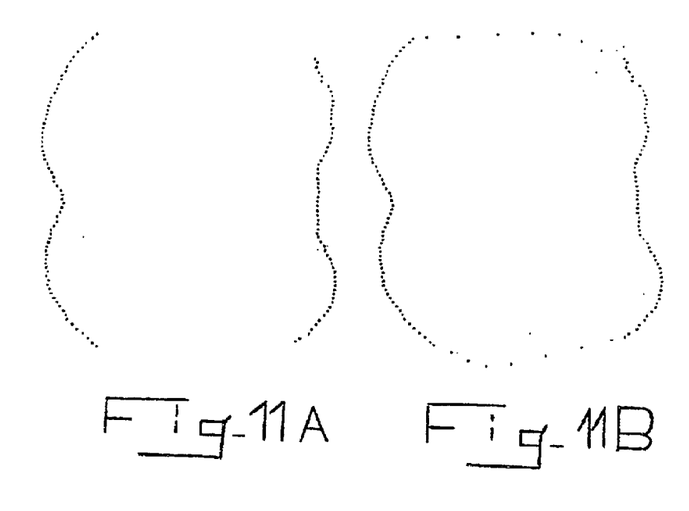
FIGS. 11A and 11B show, for a given plane at the level of the chest of a human, the front and rear cross-sections before and after joining.
Figure 12:
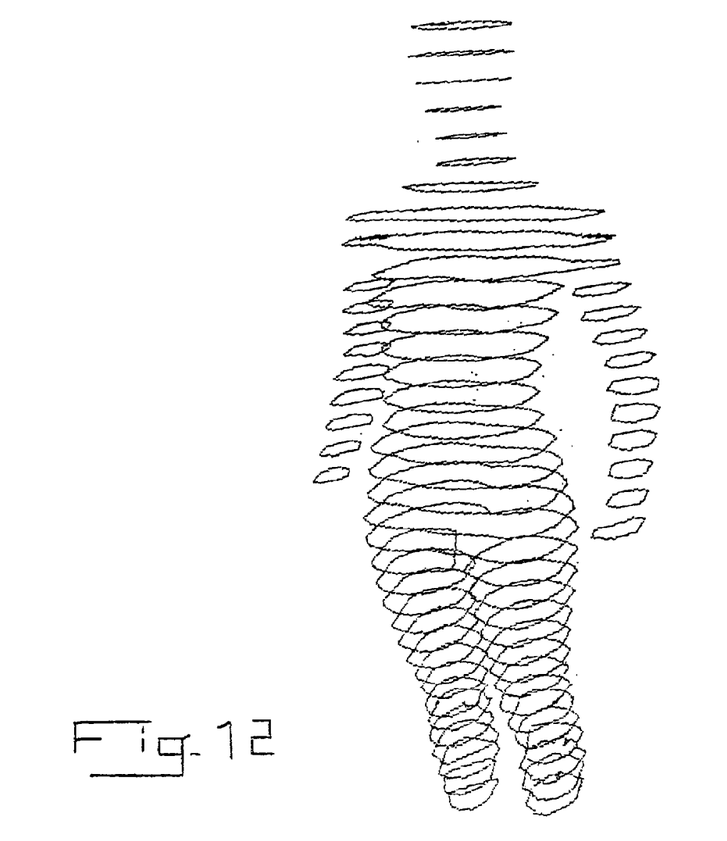
FIG. 12 is a representation of a subject in the form of a stack of cuts.

To this end, there is extracted from the points of the contour, information as to pixel width, which is used to close the corresponding slices to said points in question, by means of a cubic interpolation (FIG. 11B).

Once the slices are closed, it is necessary to stack the slices separately according to each region of the body. These assemblies can then be joined after having generated junction cuts between the zones (the junction of the left arm and the bust, for example).

The reconstruction of the finally obtained body (FIG. 12) can be exported in formats such as those known by the designations DXF (for Computer Assisted Design CAD), STL (for rapid prototyping) or AAOP (for medical CAD). These formats permit the use of the reconstruction in CAD or for rapid prototyping of prostheses for example. It is easy to imagine that the data acquired will be also transmitted to a custom tailor via the Internet.

The reconstructed body can above all serve for taking measurements. This taking of measurements is considerably simplified relative to the existing systems deforming a generic mannequin. Thus, it is a matter within the scope of the invention of measuring circumferences and lengths on this body, based on precise points such as the projection of the buttocks, the bosom, below the arm, etc.

These points are determined in collaboration between the contours and the reconstructed body in the form of a three-dimensional representation. This correlation is possible because the image coordinates of the points of the fringes have been preserved. There can thus be coordinated the points of the contour with the points of the acquired surfaces, and vice versa. The contours serve to preposition certain points that are not visible on the reconstructed body or more easily identical on the silhouette, such as the armpit, the crotch or the base of the neck, for example. The reconstructed body itself serves to detect the projecting points or breaks in the slope in the delimited zones, thanks to points characteristic of the contours. Given that the points maintain their original level of gray all during processing, the reconstructed body also permits detecting marks corresponding for example to the navel or a bosom.

For the major part of the circumferential measurements, it suffices to generate a slice at a predetermined position on the reconstructed body then to measure the length of its convex envelope. This is the case for example for the periphery of the bosom which corresponds to the length of the convex envelope of the horizontal cut passing through the nipples. The convex envelope of the cuts can be established according to the so-called Graham approach, applied in the plane of the cut.

Figure 15:
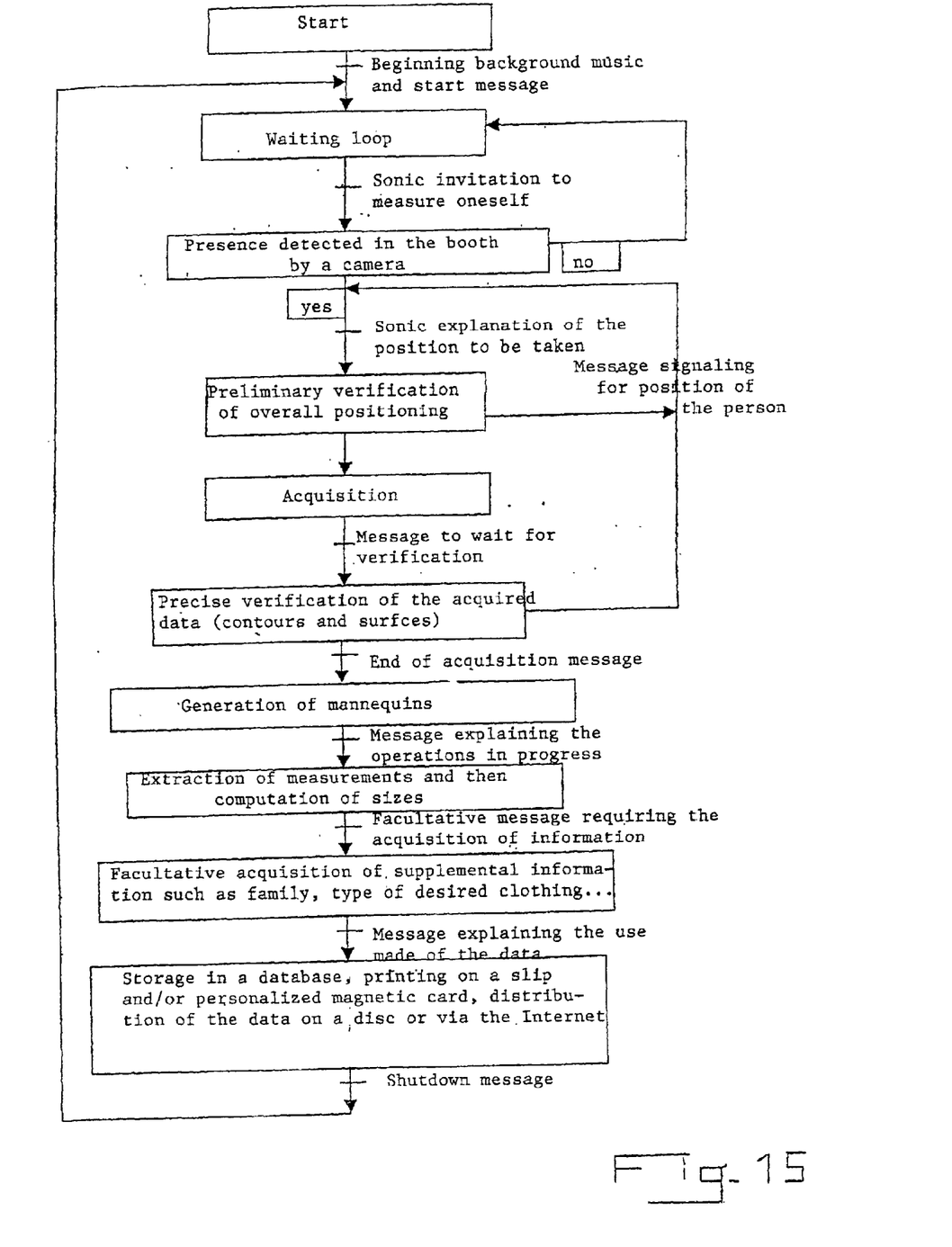

By way of example, a flow sheet representing the normal course of an acquisition session is shown in the accompanying FIG. 15.

Of course, the invention is not limited to the embodiments described and shown in the accompanying drawings. Modifications remain possible, particularly as to the construction of various elements or by substitution of technical equivalents, without thereby departing from the scope of the invention.

What is claimed is:

1. Automatic installation for the acquisition of three-dimensional shapes and for taking measurements of subjects, comprising at least one unit for projecting fringes, and at least one unit for rapidly taking views, as well as a control unit for the installation and for processing the acquired views, characterized in that said units (4, 5) for projection and taking views are gathered in at least one acquisition head and in that said installation (1) also comprises, on the one hand, several markers and several reference projection surfaces (8) surrounding the zone (9) of acquiring and measuring receiving the subject (2) to be acquired and located in the field of vision of the at least one unit for taking views and, on the other hand, means (10) for generating a temporary light wall opposite said at least one acquisition head relative to the acquisition zone (9).

2. Installation according to claim 1, characterized in that the acquisition zone (9) consists in a substantially parallelepipedal volume, the markers (7) being disposed at known positions of the control and processing unit (6) along several lateral alignments in the direction of taking the view and in two parallel spaced planes (P, P') delimiting the upper and lower surfaces of said volume (9) and the reference projection surfaces (8), undeformed consisting in vertical scales connecting the two mentioned planes (P, P') at the level of four vertical edges of the acquisition zone (9), the information supplied by the markers (7) and the projection surfaces (8) on the different views being used by the unit (6) at each acquisition of a view and for standardizing the installation (1).

3. Installation according to claim 1, characterized in that it comprises two acquisition heads (3) located in opposition on opposite sides of the acquisition zone (9), and that each of said heads (3) encloses in its field of vision all of the markers (7) and the projection surfaces (8) and in that with each of said heads (3) is associated a means (10) for generating a corresponding light wall, the arrangement of at least one of the markers (7) and the projection surfaces (8) permitting determining the upper and lower ends of the acquisition zone (9) and the orientation of this latter.

4. Installation according to claim 1, characterized in that it comprises four acquisition heads (3) gathered in two pairs of heads located in opposition on opposite sides of the acquisition zone (9), and in that one head, located in a lower position, of each of the pairs of mentioned heads encloses in its field of projection and of vision a lower portion of the acquisition volume (9) and that the other head, located in an upper position, of each of said pairs of heads, encloses an upper portion of said volume (9), complementary to and partially overlapping the mentioned lower portion, said lower heads, respectively upper heads, enclosing, moreover, lower markers (7) respectively upper markers, and lower portions, respectively upper portions, of the reference projection surfaces (8).

5. Installation according to claim 1, characterized in that it comprises at least three acquisition heads (3) disposed in a Y shape in the booth forming the installation (1).

6. Installation according to claim 1, characterized in that it comprises at least four acquisition heads (3) disposed in an X in the booth forming the installation (1).

7. Installation according to claim 1, characterized in that the means (10) for generating a wall of light consist of electronic flashes whose triggering is synchronized with that of the unit for taking views opposite it relative to the acquisition zone (9), this unit for taking views consisting of a digital video camera.

8. Installation according to claim 1, characterized in that alternate black and white fringes are produced by the units for projection (4) by means of electronic flashes associated with projection objectives without geometric deformation and synchronized as to triggering with the units (5) for taking views of the corresponding acquisition heads (3), the black fringes having a width greater than that of the white fringes, the ratio of the width of the black fringes/white fringes being comprised between 1.1 and 1.5.

9. Installation according to claim 1, characterized in that each of networks of projected horizontal fringes comprises at least two white fringes (FR1, FR2, FR3) mutually spaced apart, having widths substantially greater than those of the other fringes, and serving as reference fringes for referencing and identifying the other fringes.

10. Installation according to claim 9, characterized in that each of the networks of fringes comprises three reference fringes (FR1, FR2, FR3) disposed asymmetrically in the design of the network in question one of said reference fringes (FR1) being located for projection at about a third of the height of the volume formed by the acquisition zone (9) and at least one other (FR2) for projection at about two-thirds of the height of the volume formed by said zone (9).

11. Automatic process for substantially instantaneous acquisition of three-dimensional shapes and taking measurements of subjects, characterized in that it consists essentially in placing a subject (2) in an acquisition zone (9), this subject (2) being disposed in a given position and this zone (9) comprising markers (7) and reference projection surfaces (B), located in the fields of vision of the acquisition heads (3) of views of said subject (2) and constituting permanent standardization references, for carrying out the acquisition of a so-called front view comprising, on the one hand, taking a first front image of the subject (2) by means of a first unit (5) for taking views, in synchronism with an illumination creating a wall of light behind the subject (2) by means of a first means (10) for generating a wall of light, for the acquisition of a first silhouette contour and, on the other hand, for taking a second front image of the subject (2) by means of said first unit (5) for taking images in synchronism with the projection of a network of horizontal fringes by means of a first projection unit (4) on the front surface of the subject (2), then carrying out the acquisition of a so-called rear view in a direction opposite the direction of the front view, said acquisition comprising, on the one hand, taking a first rear view image of the subject (2) by means of a second unit (5) for taking views in synchronism with illumination creating a wall of light in front of the subject (2) by means of a second means (10) for generating a wall of light, for the acquisition of a second silhouette contour, and, on the other hand, taking a second image of the back of the subject (2) by means of said second unit (5) for taking views in synchronism with the projection of a network of horizontal fringes by means of a second projection unit (4) on the rear surface of the subject (2) and, finally, processing, by means of a suitable control and processing unit (6), the images and views acquired by correlation and exploitation of the different information supplied by it for the construction of a three-dimensional representation of the subject (2), for the extraction of measurements in one or more of predetermined categories.

12. Process according to claim 11, characterized in that the projected networks of fringes each comprise luminous reference fringes (FR1, FR2, FR3) distributed asymmetrically in the design of the network in question and having a width substantially greater than that of the other fringes and in that the taking of images is carried out in a sequential manner over an interval of total acquisition times sufficiently small to avoid the need to take into account possible movement of the subject (2).

13. Process according to claim 11, characterized in that the operation of processing consists in isolating surface images acquired by projection of fringes by means of corresponding images acquired in silhouette, then displaying and locating the fringes on the images by spatial filtration, by determining, analyzing and locating, and if desired extrapolating, the upper and lower ends of the gathered signal along a plurality of vertical lines, then identifying the different fringes, after reconstruction from fragments of fringes, and the reference fringes (FR1, FR2, FR3), counting these fringes and finally propagating the count to all the fringes contained in the isolated representations of the subject.

14. Process according to claim 13, characterized in that the identification of the fragments of fringes consists in establishing vertical adjacency relationships between consecutive fragments in the vertical direction of the views and in quantifying these relationships as a function of the length or size of overlap between two adjacent fragments, of the mean distance between two adjacent fragments, and of the respective colors of these latter.

15. Process according to claim 13, characterized in that the propagation of the counting of the fringes, after identification and counting of the reference fringes (FR1, FR2, FR3), consists in defining search paths beginning at the top of each representation of the subject (2) on the surface images in the form of isolated fringe images and extending to the ends of the different ramifications of the representation of the subject (2).

16. Process according to claim 13, characterized in that the construction of the three-dimensional representation consists, after identification and numbering on the isolated surface images acquired by projection of fringes in front and rear views, in generating representations, in the form of stacks of slices, of different separate and complementary zones of the subject (2), zones determined by means of characteristic points located on the contours obtained from silhouette views, in assembling together, for each of the mentioned separate zones, the two corresponding half shells representing the front and rear views, in the form of stacks of slices, the given zone of the subject (2) and, finally, in reconstituting a total three-dimensional volumetric representation by assembling the stacks of slices representing the different separate zones of the subject (2).

17. Process according to claim 11, characterized in that it consists in carrying out, in the course of each acquisition of a view, a step of automatic standardization on the basis of information supplied by the markers (7) and the reference projection surfaces (8) on the different images collected and used by the unit (6).

18. Process according to claim 11, characterized in that it also consists in carrying out, after rotation of the subject (2) by 90° about a vertical axis, the taking of a profile view by means of a view-taking unit (3) triggered in synchronism with a means (10) for generating a corresponding opposite wall of light, so as to acquire the contour of the silhouette of the subject (2) in profile view.

* * * * *